United States Patent
Xu

(10) Patent No.: US 7,759,332 B2
(45) Date of Patent: Jul. 20, 2010

(54) CYTOTROPIC HETEROGENEOUS MOLECULAR LIPIDS (CHML), METHOD OF PREPARATION, AND METHODS OF TREATING PATIENTS WITH MULTIPLE CANCERS

(75) Inventor: Zheng Xu, Vienna, VA (US)

(73) Assignee: Glory F & D Co., Ltd., Vienna ( * ) Notice: Subject to any disclaimer, the term of this patent is extended or adjusted under 35 U.S.C. 154(b) by 0 days.

(21) Appl. No.: 11/882,758

(22) Filed: Aug. 3, 2007

(65) Prior Publication Data

US 2008/0032957 A1 Feb. 7, 2008

Related U.S. Application Data

(60) Provisional application No. 60/835,446, filed on Aug. 4, 2006.

(51) Int. Cl.
*A61K 45/00* (2006.01)
*A61K 9/127* (2006.01)
*A61K 31/355* (2006.01)
*A61K 31/20* (2006.01)
*A01N 37/00* (2006.01)
*A01N 43/00* (2006.01)
*A01N 37/08* (2006.01)

(52) U.S. Cl. ............... 514/183; 514/167; 514/168; 514/458; 514/560; 514/558; 514/573

(58) Field of Classification Search ............ 424/450; 514/167, 168, 458, 560, 183, 558, 573
See application file for complete search history.

(56) References Cited

U.S. PATENT DOCUMENTS 5,260,067 A 11/1993 Zheng
5,874,235 A * 2/1999 Chan et al. ............ 435/18
6,340,705 B1 * 1/2002 Obukowicz et al. ...... 514/560
6,759,416 B2 * 7/2004 Wang .................. 514/283
2003/0022938 A1 * 1/2003 Burstein et al. ......... 514/558

OTHER PUBLICATIONS

Allison. Squalene and squalene emulsions as adjuvants. Methods, 19, 87-93, 1999.*
Dayton, Cells by design, New Scientist, vol. 3, pp. 42-44, 1989.
Marx, Liposomes: Research Applications Grow, Science, vol. 199, pp. 1056-1057, 1978.
Alving, Liposome techniques in cell biology. Nature, vol. 330, pp. 189-190, 1987.
Gregoriadis, The Carrier Potential of Liposomes in Biology and Medicine, New England Journal of Medicine, vol. 295, No. 14, pp. 704-710, pp. 765-770, 1976.

* cited by examiner

*Primary Examiner*—Brandon J Fetterolf
*Assistant Examiner*—Anna Pagonakis
(74) *Attorney, Agent, or Firm*—Birch, Stewart, Kolasch & Birch, LLP

(57) ABSTRACT

Cytotropic Heterogeneous Molecular Lipids (CHML) are used to treat patients with multiple cancers. Numerous studies have been conducted in cellular, animal, pre-clinical and clinical trials. Results showed that CHML, as a biological molecular missile, can easily penetrate through the target cancerous cells to perform programmed cancer cell death (cancer apoptosis). Furthermore, CHML has produced anti-cancer angiogenesis and induced immune function increase. CHML was used to treat 592 patients with cancers in clinical trials. Results confirmed the following advantages of CHML treatment: non-toxicity, high response rate, high quality of life, and high survival rate for these patients. The protocols include local injection, arterial drip and intravenous drip to treat cancers of liver, lung, skin, breast, brain glioma, colon and rectum, stomach, head and neck, leukemia, malignant lymphoma, sarcoma, malignant melanoma, myeloma, and metastasis cancers, etc.

16 Claims, No Drawings

CYTOTROPIC HETEROGENEOUS MOLECULAR LIPIDS (CHML), METHOD OF PREPARATION, AND METHODS OF TREATING PATIENTS WITH MULTIPLE CANCERS

CROSS-REFERENCE TO RELATED APPLICATIONS

The present application claims priority under 35 USC 119(e) to U.S. Provisional Patent Application No. 60/835,446 filed on Aug. 4, 2006 the entire contents of which are hereby incorporated by reference.

BACKGROUND OF THE INVENTION

1. Field of the Invention

Cytotropic Heterogeneous Molecular Lipids (CHML) penetrate through target cancerous cells to perform programmed cancer cell death (cancer apoptosis). Furthermore, CHML has produced anti-cancer angiogenesis and induced immune function increase.

2. Description of the Related Art

Phosphatide has been known to form small multilayered capsules while dispersing in water, and discovered that each layer of bimolecular lipids in a multilayer cyst is separated by water, the thickness of each layer being about 40 Å. This kind of capsule formed of microparticles, having a structure similar to a biomembrane, is termed a liposome.

Since liposomes form a hydrophilic and/or lipophilic container-like structures, these structures may envelop molecules and ions which are soluble in water or lipid. Due to these specific characteristics, liposomes can be useful as carriers, especially for pharmaceuticals. Further, liposomes may alter the mechanism of pharmaceutical metabolism and selectively transport the pharmaceutical to the "target", then release the pharmaceutical at the proper part of tissues to be cured. Thus, toxicity to normal cells can be reduced and the curative effect, i.e. attack on deleterious cells, can be greatly enhanced.

In addition, there is another specific property in that the pharmaceutical enveloped by the liposome may be slowly released into local sites whether entering into blood circulation or combining with cells and tissues, even entering into cells through pinocytosis. With the slow release mechanism of liposomes, the half-life of the effective pharmaceutical is prolonged and the therapeutic effect is obviously improved. Furthermore, liposomes are made from natural phosphatides and cholesterols, having low toxicity, free from immunogens and with suitable bio-compatibility and bio-degradable properties.

In the related art, liposomes have been formed from phosphatide as a skeleton material and additives. Phosphatide is an amphoteric compound possessing hydrophilic and lipophilic radicals, including natural phosphatide (lecithin and soybean lecithin) and synthetic phosphatide (such as phosphalidyl choline, dipalmitol phosphatidyl choline and distearyl phosphatidyl choline). These phosphatides provide two hydrophilic chains. They form liposomes of bimolecular layers in water, no matter how the structure of the hydrophilic radical is. The additives used have been, for example, cholesterol, octadecamine and phosphatidate, etc. Although cholesterol is useful for regulating the flowability and permeability of a bimolecular layer, cholesterol is not healthy for human beings. Octadecamine and phosphatidate may be used to alter the surface electrical charges of a liposome. The components of a polythase liposome may be phosphatide, oleic acid, cholesterol and nonionic surfactants such as PVP (polyvinyl pyrrolidone).

Liposomes are known as drug carriers, as models of biomembranes, and methods of preparation. Polyphase liposomes are formed after the phosphatides contact with water. Formation is due to the action if its polar group and hydrophobic group which lead to the formation of poly bimolecular layers of a closed type spherical structure. The water layer is laid between the bimolecular layers as the water-soluble drugs are enveloped into it, the liposoluble pharmaceutical being enveloped in the bimolecular layers. Many factors as surface characteristics, particle sizes, differences in forms, surface electrical charges of the liposome can effect the stability in vivo and the percentages of enveloped pharmaceutical. The factors depend upon the components of phosphatides and methods of preparation.

However, the chemical properties of phosphatide with unsaturated fatty acid chain, such as of lecithin and soya bean lecithin, are prone to displaying insufficient stability. Phosphatide is susceptible to oxidation and hydrolysis. Thus, peroxides such as propanediol and lysophosphatide are produced. The oxidation of lecithin will subject the membrane formed to decreased flowability and increased stability and negative electrical charge conditions. Thus leakage of drugs will be promoted so that retaining of drugs will become less and the liposome will be easily aggregated and precipitated, thereby producing toxicity. Therefore, it would be advantageous if lecithin used as a membrane material should have high purity and an oxidation index of less than 0.2.

In the preparation of liposomes, it is a difficult problem to envelope a large quantity of drug. For example, where the liposolubility and aqueous solubility of the pharmaceutical are both low, the envelopment quantity of the drug will be less. Also, when the molecule of the drug is small and easily subject to percolation, the envelopment quantity of the drug will be weaker. As a result, conventional art liposome technology has been found to lack sufficient stability to deliver substances associated with rigorous therapeutic regimens. Particularly, suitable vehicles for carrying, cancer-fighting drug molecules are greatly desired.

Presently, acceptable medical treatment for different forms of cancer includes: surgery, chemotherapy, radiation and biological therapies. Recent advances in biotechnology have led to an improved understanding of the different biological functions that control the proliferation of malignant cells and the particular genetic defects which can lead to tumor growth.

Chemotherapeutic drugs are intended to destroy cancer cells, but are largely non-selective in their eradication of the body's cells. Research is currently focusing on drugs that are able to selectively kill cancer cells, which exhibits less toxicity to normal cells.

As a result, liposome technology offers advanced technology that can be used to create new cancer therapies.

SUMMARY OF THE INVENTION

Accordingly, it is an object of the invention to overcome the disadvantages associated with the related art liposome technology.

The invention, in part, pertains to the pharmaceutical formulations formed from Cytotropic Heterogeneous Molecular Lipids (CHML). In the invention, CHML produces anti-cancer angiogenesis and induces immune function increase. Experimental results have shown the following advantages of CHML treatment: non-toxicity, high response rate, high quality of life, and high survival rate for the patients. The protocols for application include local injection, arterial drip and intravenous drip to treat cancers of liver, lung, skin, breast, brain glioma, colon and rectum, stomach, head and neck, leukemia, malignant lymphoma, sarcoma, malignant melanoma, myeloma, metastasis cancers, etc.

In the invention, CHML demonstrates anti-cancer effects, and is confirmed to be highly stable in extensive tests. Induction of tumor cell silicide through programmed cell death (apoptosis) has been widely used to study the mechanism of control tumor growth. Mechanism studies have confirmed that CHML is able to induce programmed cancer cell death (cancer apoptosis). CHML demonstrates relatively high specificity to attack tumor cells with relative lower cytotoxicity on normal cells as demonstrated by in vitro and in vivo experiments.

In the invention, CHML was shown to be safe at a clinically effective dosage (based upon in vitro and in vivo pharmacology studies) in normal human subjects in Phase 1 clinical studies.

It is to be understood that both the foregoing general description and the following detailed description are exemplary and explanatory and are intended to provide further explanation of the invention as claimed.

DETAILED DESCRIPTION OF THE PREFERRED EMBODIMENTS

Cytotropic Heterogeneous Molecular Lipids (CHML) have been discussed in U.S. Pat. No. 5,260,067, granted on Nov. 9, 1993. U.S. Pat. No. 5,260,067 did not present each ingredient of unsaturated fatty acids and saturated fatty acids. The present invention, however, elucidates each ingredient of unsaturated fatty acids and saturated fatty acids so as to easily obtain CHML efficacy and control CHML quality. The method of preparation in the present invention are simpler than the methods of the related art technology, thus yielding improvements in preparation methods, energy savings, cost and time. Furthermore, treatment methods for cancer patients were not presented in U.S. Pat. No. 5,260,067 because there was no formal clinical trials at that time. In the present invention, CHML has been used to treat 592 patients with cancers in clinical. Results have confirmed the advantages of CHML, including non-toxicity, high response rate, high quality of life, and high survival rate for these patients. The protocols for local injection, arterial drip and intravenous drip to treat cancers of liver, lung, skin, breast, brain glioma, colon and rectum, stomach, head and neck, leukemia, malignant lymphoma, sarcoma, malignant melanoma, myeloma, metastasis cancers, etc.

Following CHML development, new pharmaceutical compositions, new methods of preparation, and new methods of treating patients with multiple cancers were developed. Numerous studies have been conducted in cellular, animal, pre-clinical and clinical trials. Results showed that CHML, as a biological molecular missile, can easily penetrate through the target cancerous cells to perform programmed cancer cell death (cancer apoptosis). Furthermore, CHML has produced anti-cancer angiogenesis and induced immune function increase. CHML has been used to treat 592 patients with cancers in clinical trials. Results confirmed the following advantages of (CHML treatment: non-toxicity, high response rate, high quality of life, and high survival rate for these patients. The protocols for local injection, arterial drip and intravenous drip to treat cancers of liver, lung, skin, breast, brain glioma, colon and rectum, stomach, head and neck, leukemia, malignant lymphoma, sarcoma, malignant melanoma, myeloma, metastasis cancers, etc.

When considering the definitions of CHML, "Cytotropic" means that the lipids have an affinity for cytological cells, especially for the membrane structure of cancer cells. "Heterogeneous" indicates the similarity of properties of lipids in physics, chemistry and biology compare to those of the membranes of cancer cells. "Molecular" suggests the molecular size of the lipids (molecular weight of about 300) with dimensions of about $(20-30) \times (8 \times 10) \times (4 \times 6)$ Å, which is less than $\frac{1}{10}$th of the size of a liposome of the related art. Hence, this "ultra-micro missile" avoids the problem of causing systemic capillary circulation obstacles when entering the vein. This problem has been found for the average sized liposomes. "Lipids" describes the molecular composition structure and therapeutic effects provided by the invention, characteristics different from those of the conventional liposome. Thus, CHML is a novel and unique anti-cancer drug that has active orientation to penetrate into the membrane of cancerous cells and has relatively high idiosyncratic absorbing capacity by target cells.

A typical formulation of CHML for the invention is as follows:

9-12 wt. % arachidonic acid;
5-7 wt. % linolenic acid;
12-26 wt. % docosahexaenoic acid;
8-14 wt. % eicosapentaenoic acid;
30-38 wt. % oleic acid;
8-15 wt. % palmitic acid;
4-10 wt. % stearic acid;
0.7-1.5 wt. % Vitamin A;
0.3-1.0 wt. % Vitamin D;
0.8-3.1 wt. % Vitamin E; and
0.5-2.1 wt. % squalene The method of preparation is as follows:

CHML is prepared by homogenizing the compounds listed above. It is prepared into two types of medicinal products: (1) 100 grams of CHML compound/2,000 ml sterile water for injection which contains CHML 100 mg in 2 ml per ampoule; (2) 100 grams of CHML compound/4,000 ml sterile water for injection which contains CHML 250 mg in 10 ml per ampoule.

The following steps are used to prepare both medicinal products.

1. Mix and shake fully.
2. Add activated carbon.
3. Heat mixture at 100° C. to boil for 15-30 minutes.
4. Decrease temperature to 15-30° C.

The mixture was filtered through a 0.4-5 μm membrane, centrifuged and filtered through a 0.22 μm membrane, thereby obtaining two types of transparent medicinal products.

The methods of treating multiple cancers are as follows:

Local injection. The patients with visible cancers were treated were treated 35-70 mg/cm$^2$ (tumor area), 2-3 times/week. 3-4 weeks as 1 cycle, rest for 2-4 weeks and repeat; the patients with brain tumor were treated with 1.4-1.8 mg/cm$^3$ (tumor cube), 3-4 times/week, 4 weeks as 1 cycle, rest for 2-4 weeks and repeat;

Arterial drip. The patients with liver and stomach cancers were treated with 7-14 mg/kg/1 time/day, 7 times/week, 25-30 days as 1 cycle, rest for 2-4 weeks and repeat; the patients with colon and rectum cancer were treated with 7-10 mg/kg/1 time/day, 7 times/week, 10-15 days as 1 cycle, rest for 2-4 weeks and repeat; and Intravenous drip. The patients were treated with 14-28 mg/kg/1 time/day, 7 times/week, 25-40 days as 1 cycle, rest for 2-4 weeks and repeat.

One preferred method of treating multiple cancers is multiple injection to treat skin cancer, breast cancer, sarcoma, malignant melanoma, and other visible cancers. A specific treatment procedure as follows:
1. Mark tumor size, including 1 cm around the tumor.
2. Divide into 0.5 cm×0.5 cm by using methylene blue.
3. Mix fully CHML 100 mg/l ampoule, CHML 250 mg/l ampoule, 2% Lidocaine Hydrochloride Injection 5 ml, and 5% Glucose and Sodium Chloride Injection (5% GNS) 15 ml.
4. Inject evenly into each 0.5 cm² of tumor size with 0.5 ml of CHML mixed injection, total 2 times for 1 week, 3 weeks for one cycle, repeat after 2-4 week until cancer disappears completely.

Another preferred method of treating multiple cancers is brain injection to treat brain tumors. The specific treatment procedure as follows:
1. Insert an Ommaya Reservoir into tumor cavity.
2. Mixed fully CHML 100 mg/l ampoule, CHML 250 mg/l ampoule, 5% GNS 200 ml.
3. Inject with 3-10 ml of CHML mixed injection into whole tumor cavity.
4. Perform injection total 3 times for 1 week, 4 weeks for one cycle, repeat after 2-4 week until tumor disappears completely.

A preferred method of treating multiple cancers is arterial drip for treating cancers of liver and stomach. A specific treatment procedure as follows:
1. Insert an arterial catheter into a tumor artery using Digital Subtraction Angiography (DSA).
2. Drip via an arterial infusion pump.
3. Mix fully CHML 100 mg/l ampoule, CHML 250 mg/l ampoule, 5% GNS 500 ml.
4. Drip into tumor artery for 3 hours per day, 7 times a week, 25-30 days for one cycle, repeat after 2-4 weeks.

A preferred method of treating multiple cancer is arterial drip for treating cancer of colon and rectum. A specific treatment procedure as follows:
1. Insert an arterial catheter into a tumor artery using Digital Subtraction
2. Angiography (DSA).
3. Drip via an arterial infusion pump.
Mix fully CHML 100 mg/l ampoule, CHML 250 mg/l ampoule, 5% GNS 500 ml. Drip into tumor artery for 10 hours per day, 7 times a week, 10 days for one cycle, repeat after 2-4 weeks.

A preferred method of treating multiple cancer is intravenous drip. It may be used to treat cancer of lung, malignant lymphoma, leukemia myeloma, head and neck cancer, and metastasis cancer, etc.
Specific treatment procedure as follows:
1. Mix fully CHML 200-400 mg/2-4 ampoules, CHML 500-1,000 mg/2-4 ampoules, 5% GNS 400-800 ml.
2. Drip into vein for 8 hours per day, 7 times a week, 25-30 days for one cycle, repeat after 2-4 weeks.

EXAMPLES

In order to increase efficacy and reduce toxicity in cancer treatment, a novel biological medicine, CHML, was treated and evaluated for response, toxicity, quality of life, and survival rate in 592 patients with multiple cancers.

Experimental Design:

Local injection. The patients with visible cancers were treated were treated 35-70 mg/cm² (tumor area), 2-3 times/week. 3-4 weeks as 1 cycle, rest for 2-4 weeks and repeat; the patients with brain tumor were treated with 1.4-1.8 mg/cm³ (tumor cube), 3-4 times/week, 4 weeks as 1 cycle, rest for 2-4 weeks and repeat;

Arterial drip. The patients with liver and stomach were treated with 7-14 mg/kg/l time/day, 7 times/week, 25-30 days as I cycle, rest for 2-4 weeks and repeat; the patients with colon and rectum cancer were treated with 7-10 mg/kg/l time/day, 7 times/week, 10-15 days as 1 cycle, rest for 2-4 weeks and repeat; and Intravenous drip. The patients were treated with 14-28 mg/kg/l time/day, 7 times/week, 25-40 days as 1 cycle, rest for 2-4 weeks and repeat.

Summary of Results:

Response rates (CR+PR) were as follows: liver cancer 77%, lung cancer 68%, skin cancer 94%, breast cancer 83%, brain glioma 78%, colon and rectum cancer 80%, stomach cancer 50%, head and neck cancer 78%, leukemia 83%, malignant lymphoma 71%, sarcoma 43%, malignant melanoma 67%, and myeloma 50%. No (0) episodes of grade II or above adverse reactions were observed. CHML was effective and well tolerated, as no grade II or above adverse reactions occurred in this study.

A preferred CHML composition includes about 9-12 wt. % arachidonic acid, about 5-7 wt. % linolenic acid, about 12-26 wt. % docosahexaenoic acid, about 8-14 wt. % eicosapentaenoic acid, about 30-38 wt. % oleic acid, about 8-15 wt. % palmitic acid, about 4-10 wt. % stearic acid, about 0.7-1.5 wt. % Vitamin A, about 0.3-1.0 wt. % Vitamin D, about 0.8-3.1 wt. % Vitamin E and about 0.5-2.1 wt. % squalene A preferred method of preparing CHML includes homogenizing the compounds listed above. The formulation is prepared into two types of medicinal products: (1) 100 grams of CHML compound/2,000 ml sterile water for injection which contains 100 mg CHML in a 2 ml ampoule; and (2) 100 grams of CHML compound/4,000 ml sterile water for injection which contains 250 mg CHML in a 10 ml ampoule.

The following steps were used to prepare both medicinal products.
A. Mix and shake fully.
B. Add activated carbon.
C. Heat mixture at 100° C. to boil for 15-30 minutes.
D. Decrease temperature to 15-30° C.
E. Filter mixture through a 0.45 u membrane, centrifuge and filter through a 0.22 u membrane, thereby obtaining two types of transparent medicinal products.

Methods of Treating Patients with Multiple Cancers
Materials and Methods

1. CHML medicine:
    Product lot number 9709147, 9803077, 9907077, 20000707, 20010707 and 20020707 were provided by Glory F & D Co Ltd, USA according to Good Clinical Practice Standard [Ref: Food and Drug Administration (FDA), Guidance for Industry. E6 Good Clinical Practice: Consolidate Guidance, 1996]. All components of CHML were extracted from plants and animals in nature and prepared by biological lipid method. All components of CHML contain 100 mg in 2 ml per ampoule and 250 mg in 10 ml per ampoule.

2. Methods according to Good Clinical Practice Standard from FDA.
    2.1 Patient information: Cancer staging standard according to International Union Against Cancer (UICC) TNM classification of malignant tumours, World Health Organization (WHO) classification of brain tumours, and French-American-British (FAB) classification of leukemia. General information for all patients is contained in Table 1. Patient selection standards were as follows:
- A. Clinically confirmed (by pathological or biopsy) cancer diagnosis. Measurable tumor size by X-ray, CT, NRI, or ultrasonography. No chemotherapy or no radiation<4 weeks prior to study.
- B. Performance scale (Kamofsky): ≧60.
- C. Estimation for survival time: ≧3 months.
- D. Age: Adult, 14-81 year-old.

2.2 Adequate major organ functions (heart, lung, liver, kidney, stomach, colon and bone marrow) according to WHO Toxicity Guidelines grade 0-I standards[14].

2.3 Patient must be understood the following ethic issue. Patient, except the patient who was evaluated and reported the cancer is late stage and no current available methodology for his or her treatment by the other oncology experts, can potentially be given other effective treatments that are available in the participating hospital and may be done the current available methodology.

2.4 All patients must sign an informed consent.

2.5 Administration and dosage:
- A. Local injection. It is used to treat skin cancer, breast cancer, sarcoma, malignant melanoma, and other visible cancers. Specific treatment procedure as follow s:
  - a. Mark tumor size, including 1 cm around the tumor.
  - b. Divide into 0.5 cm×0.5 cm by using methylene blue.
  - c. Mix fully CHML 100 mg/l ampoule, CHML 250 mg/l ampoule, 2% Lidocaine Hydrochloride Injection 5 ml, and 5% Glucose and Sodium Chloride Injection (5% GNS) 15 ml.
  - d. Inject evenly into each 0.5 cm$^2$ of tumor size with 0.5 ml of CHML mixed injection, inject on Mondays and Thursdays, total 2 times for 1 week, 3 weeks for one cycle, repeat after 2-4 week until cancer disappears completely.
- B. Brain injection. It is used to treat brain tumor. Specific treatment procedure as follows:
  - a. Insert an Ommaya Reservoir into tumor cavity.
  - b. Mixed fully CHML 100 mg/l ampoule, CHML 250 mg/l ampoule, 5% GNS 200 ml.
  - c. Inject with 3-100 ml of CHML mixed injection into whole tumor cavity.
  - d. Inject on Mondays, Wednesdays and Fridays, total 3 times for 1 week, 4 weeks for one cycle, repeat after 2-4 week until tumor disappears completely.
- C. Arterial drip for treating cancers of liver and stomach. Specific treatment procedure as follows:
  - a. Insert an arterial catheter into a tumor artery using Digital Subtraction Angiography (DSA).
  - b. Drip via an arterial infusion pump.
  - c. Mix fully CHML 100 mg/l ampoule, CHML 250 mg/l ampoule, 5% GNS 500 ml.
  - d. Drip into tumor artery for 8 hours per day, 7 times a week, 25-30 days for one cycle, repeat after 2-4 weeks.
- D. Arterial drip for treating cancer of colon and rectum. Specific treatment procedure as follows:
  - a. Insert an arterial catheter into a tumor artery using Digital Subtraction Angiography (DSA).
  - b. Drip via an arterial infusion pump.
  - c. Mix fully CHML 100 mg/l ampoule, CHML 250 mg/l ampoule, 5% GNS 500 ml.
  - e. Drip into tumor artery for 10 hours per day, 7 times a week, 10 days for one cycle, repeat after 2-4 weeks.
- E. Intravenous drip. It is used to treat cancer of lung, malignant lymphoma, leukemia myeloma, head and neck cancer, and metastasis cancer, etc. Specific treatment procedure as follows:
  - a. Mix fully CHML 200-400 mg/2-4 ampoules, CHML 500-1,000 mg/2-4 ampoules, 5% GNS 400-800 ml.
  - b. Drip into vein for 8 hours per day, 7 times a week, 25-30 days for one cycle, repeat after 2-4 weeks.

2.6 Response standard is according to WHO reporting results of cancer treatment: A complete response (CR) is defined as the complete disappearance of the entire tumor lasting for more than 4 weeks. A partial response (PR) is defined as a 50% or great reduction in the product of the two greatest perpendicular diameters or at least a 30% reduction in hepatomegaly and without the appearance of new lesions, lasting for more than 4 weeks. Any reduction and/or duration of response insufficient for classification as a PR is classified as a minor response (MR). No change (NC) is defined as no change or up to 25% progression in tumor size 4 weeks after the beginning of treatment. Progressive disease (PD) in defined as a greater than 25% increase in tumor measurements or the appearance of new lesions within 4 weeks after the beginning of treatment.

2.7 Toxicity criteria and examination according to National Cancer Institute (NCI) Guidelines for reporting of adverse reaction. All patients were examined as follows.
- A. General health: Evaluate weight, diet, sleep, nausea, vomiting, diarrhea, and alopecia, every day, and follow up for 3 months. Reevaluated abnormal reporting patients daily.
- B. Blood test: Week one—evaluate white blood cell (WBC), platelet (PLT), and hemoglobin (Hgb) levels upon completion of treatment, and one week post Treatment. If normal continue test bi-weekly for 3 months.
- C. Liver function: Week one—evaluate glutamic oxaloacetic transaminase (SGOT), glutamic-pyruvic transaminase (SGPT), alkaline phosphatase (AKP) and total bilirubin in serum (TBIL) levels upon completion of treatment, and one week post treatment. If normal continue test bi-weekly for 3 months.
- D. Kidney function: Week one—evaluate creatinine and proteinuria levels upon completion of treatment, and one-week post treatment. If normal, continue test bi-weekly for 3 months.
- E. Respiratory system: Evaluate for abnormal pulmonary symptoms (BRMP) and pulmonary function (BRMP). If abnormal, reevaluate daily; if normal continue test bi-weekly for 3 months.
- F. Cardiovascular system: Evaluate for cardiac dysrhythmias, cardiac function, cardiac ischemia and blood pressure. If abnormal, reevaluate daily; if normal continue test bi-weekly for 3 months.
- G. Nervous system: Evaluate neurosensory, neuromotor, neurocortical, neurocerebellar, neuromood, neuroheadache, neuroconstipation, neurohearing, and neurovision. If abnormal, reevaluate daily; if normal continue test bi-weekly for 3 months.

Results
1. Efficacy: A total of 1,424 cycles were administered. 352 patients received 2 cycles and 240 patients received 3 cycles. A six-month follow-up for each patient (Table 3-15). Patients were evaluated for response that is shown in Table 2 and in detail in Table 3-15. The response rates for patients with following cancer types are as follows: 135 patients with liver cancer 77%, 102 patients with lung cancer 68%, 67 patients with skin cancer 94%, 65 patients with breast cancer 83%, 65 patients with brain glioma 78%, 61 patients with colon and rectum cancer 80%, 30 patients with stomach cancer 50%, 23 patients with head and neck cancer 78%, 18 patients with leukemia 83%, 14 patients with malignant lymphoma 71%, 7 patients with sarcoma 43%, 3 patients with malignant melanoma. 67%, and 2 patients with myeloma 50%.

2. Toxicity: A total of 1,424 cycles were administered. 352 patients received 2 cycles and 240 patients received 3 cycles. A six-month follow-up for each patient (Table 3-15). Patients were evaluated for toxicity that is shown in detail in Table 3-15. As noted in Table 3-15, 7-patients experienced Grade I nausea, and 11-patients experienced elevated Grade I SGPT in liver function.

CONCLUSION 592 patients, clinical diagnosed with the cancers of liver, lung, skin, breast, brain glioma, colon and rectum, stomach, head and neck, leukemia, malignant lymphoma, sarcoma, malignant melanoma, myeloma, and metastasis cancers, were treated and evaluated for response and toxicity.

CHML was effective and well tolerated, as no grade II or above adverse reactions occurred in this study.

REFERENCES

1. Vincent T. DeVita, Jr. Samuel Hellman, Steven A. Rosenbery. (1997). Pharmacology of cancer chemotherapy. Cancer principles & practice of oncology. 19:375-498.
2. Vincent T. DeVita, Jr. Samuel Hellman, Steven A. Rosenbery. (1997). Adverse effects of treatment. Cancer principles & practice of oncology. 53:2705-2806.
3. Wyllie, A. H., Kerr, J. F. R., and Currie, A. R. (1980). Int. Rev. Cytol. 68:251-305.
4. Gwyn T. Williams. (1991). Programmed cell death: Apoptosis and oncogenesis. Cell. 65:1097-1098.
5. Martin C. Raff. (1992). Social controls on cell survival and cell death. Nature. 356:397-400.
6. Michael B. Kastan, Zhan Q, Wafik S. El-Deiry, France Carrier, Tyler Jacks, William V. Wash, Beverly S. Plunkett, Bert Vogelstein, Albert J. Formace, Jr. (1992). A mammalian cell cycle checkpoint pathway utilizing p53 and GADD45 is defective in ataxia-telangiectasia. Cell. 71:587-597.
7. Zhan Q, Insoo Bae, Michael B. Kastan, and Albert J. Formace, Jr. (1994). The p53-dependent r-ray response of GADD45. Cancer Res. 54:2755-2760.
8. Zhan Q and Xu Z. (1999). CHML suppresses cell growth and induces apoptosis in multiple human tumor lines. Anticancer Res. 19:2893-2899.
9. Zhan Q, Zhao S C and Xu Z (2001). Antitumor activity of cytotropic heterogeneous molecular lipids (CHML) on human breast cancer xenograft in nude mice. Anticancer Res. 21:2477-2482.
10. CHML documentation for application of Cytotropic Heterogeneous Molecular Lipids (CHML) in normal human subjects, Phase 1, 1996.
11. Food and Drug Administration (FDA). (1996). Guidance for Industry. E6 Good Clinical Practice: Consolidate Guidance.
12. David S Fishcher, M. Tish Knobf, Henry J. Durivage. (1993). Clinical trials. The cancer chemotherapy handbook. 30-36.
13. Vincent T. DeVita, Jr. Samuel Hellman, Steven A. Rosenbery. (1997). Clinical trials in cancer. Cancer principles & practice of oncology. 20:513-541.
14. Michael C. Perry. (1992). Appendix/WHO toxicity guidelines. The chemotherapy source book. 1132-1140.
15. World Health Organization (WHO). (1979). WHO handbook for reporting results of cancer treatment.
16. David S Fishcher, M. Tish Knobf, Henry J. Durivage. (1993). Common toxicity criteria. The cancer chemotherapy handbook. Appendix: 501-505.
17. National Cancer Institute (1988). Guidelines for reporting of adverse reaction. Bethesda, Md.: Division of cancer treatment. National Cancer Institute.
18. L. H. Sobin and Ch. Wittekind. (1997). International Union Against Cancer (UICC), TNM classification of malignant tumours. Fifth edition.
19. Kleihues P, Burger P C, Scheithauer B W. (1993). The New World Health Organization (WHO) classification of brain tumours. Brain Pathol. 3:255.
20. Bennett J M, Catovsky D, Daniel M T, Flandrin G, Galton D A G, Gralnick H R, et al. (1976). Proposals for the classification of the acute leukaemias. Br J Haematol. 33:451.

TABLE 1

CHML Clinical Trials-General Patient History

| Item | Case No. | % |
|---|---|---|
| Total case no. | 592 | |
| no. case evaluated for efficacy | 592 | 100 |
| no. cases evaluated for toxicity | 592 | 100 |
| Sex | | |
| male | 381 | 64 |
| female | 211 | 36 |
| Age | | |
| 10-20 | 17 | 3 |
| 21-30 | 32 | 4 |
| 31-40 | 84 | 11 |
| 41-50 | 149 | 24 |
| 51-60 | 153 | 27 |
| 61-70 | 124 | 22 |
| Over 70 | 33 | 8 |
| Performance scale (Karnofsky) | | |
| 100 | 5 | <1 |
| 90 | 76 | 13 |
| 80 | 117 | 20 |
| 70 | 188 | 32 |
| 60 | 206 | 35 |
| No. of prior chemotherapy (n = 592) | 292 | 49 |
| No. of prior radiation (n = 592) | 136 | 23 |

TABLE 2

CHML Clinical Trials-Efficacy

| Cancer Type | Case No. | CR | PR | MR | NC | PD | (CR + PR) % |
|---|---|---|---|---|---|---|---|
| Liver cancer | 135 | 33 | 71 | 15 | 11 | 5 | 77 |
| Lung cancer | 102 | 27 | 42 | 15 | 11 | 7 | 68 |
| Skin cancer | 67 | 44 | 19 | 4 | 0 | 0 | 94 |
| Breast cancer | 65 | 30 | 24 | 5 | 4 | 2 | 83 |
| Brain glioma | 65 | 23 | 28 | 9 | 5 | 0 | 78 |
| Colon & rectum cancer | 61 | 20 | 29 | 7 | 4 | 1 | 80 |
| Stomach cancer | 30 | 3 | 12 | 7 | 6 | 2 | 50 |
| Head and neck | 23 | 4 | 14 | 3 | 2 | 0 | 78 |
| Leukemia | 18 | 4 | 11 | 2 | 1 | 0 | 83 |
| Malignant lymphoma | 14 | 8 | 2 | 2 | 0 | 2 | 71 |
| Sarcoma | 7 | 1 | 2 | 2 | 1 | 1 | 43 |
| Malignant melanoma | 3 | 1 | 1 | 1 | 0 | 0 | 67 |
| Myeloma | 2 | 0 | 1 | 1 | 0 | 0 | 50 |

TABLE 3

Patient characteristics of liver cancer

| Patient[d] | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 1 | 55 | M | 80 | 2 | IVA | CT | 2 | NC | | SB |
| 2 | 61 | M | 70 | 2.5 | IIIB | CT | 3 | PR | | SB |
| 3 | 52 | M | 80 | 0.25 | IIIB | | 3 | CR | | SB |
| 4 | 48 | M | 70 | 2 | IVA | CT | 2 | PR | | SB |
| 5 | 56 | M | 60 | 10 | IIIB | CT | 2 | MR | | SB |
| 6 | 72 | M | 80 | 3 | IIIB | CT | 2 | PR | | SB |
| 7M | 53 | M | 70 | 0.5 | IVA | | 2 | MR | SGPT[+], I | SB |
| 8M | 25 | M | 70 | 6.5 | IVA | S, CT | 3 | PR | | SB |
| 9 | 50 | M | 70 | 3.5 | IIIB | CT | 3 | CR | | SB |
| 10M | 48 | M | 60 | 2 | IIIB | CT | 3 | PR | | SB |
| 11 | 37 | M | 90 | 3.5 | IIIB | CT | 2 | PR | | SB |
| 12 | 56 | M | 80 | 0.25 | IVA | | 3 | PR | | SB |
| 13M | 59 | M | 60 | 2 | IVA | CT | 3 | PR | | SB |
| 14M | 68 | M | 60 | 3 | IVB | CT | 2 | PD | | RL, MT |
| 15M | 65 | M | 80 | 3.5 | IIIB | CT | 3 | CR | | SB |
| 16M | 45 | F | 80 | 3 | IIIA | CT | 2 | PR | | SB |
| 17M | 64 | F | 60 | 5 | IIIB | CT | 2 | MR | | SB |
| 18 | 49 | M | 70 | 2 | IIIB | CT | 2 | NC | | RL |
| 19 | 53 | M | 90 | 3 | IIIB | CT | 2 | PR | | SB |
| 20 | 60 | M | 70 | 2 | IVA | CT | 3 | PR | | SB |
| 21 | 44 | M | 70 | 2 | IIIA | CT | 2 | PR | | SB |
| 22 | 53 | M | 80 | 5.5 | IVA | S, CT | 3 | PR | | SB |
| 23 | 54 | M | 70 | 7.5 | IIIB | S, CT | 2 | PR | | SB |
| 24M | 40 | M | 60 | 23 | IIIA | S, CT, RT | 2 | MR | | SB |
| 25 | 61 | M | 70 | 0.5 | IIIB | | 2 | PR | | SB |
| 26 | 49 | M | 80 | 3 | IIIB | CT | 2 | PR | | SB |
| 27 | 52 | M | 70 | 3.5 | IIIA | CT | 3 | PR | | SB |
| 28 | 65 | M | 70 | 0.25 | IVA | | 2 | MR | | MT |
| 29M | 52 | F | 60 | 2.5 | IVA | CT | 2 | NC | | RL |
| 30 | 52 | M | 70 | 0.5 | IIIB | | 2 | NC | | SB |
| 31 | 65 | M | 80 | 2 | IIIB | CT | 3 | PR | | SB |
| 32M | 52 | M | 80 | 24 | IIIA | S, CT | 3 | CR | | SB |
| 33 | 37 | M | 60 | 0.5 | IVB | | 2 | PD | NS, I | RL, MT |
| 34 | 66 | M | 80 | 4 | IIIB | CT | 2 | PR | | SB |
| 35 | 70 | M | 80 | 24 | IIIA | S, CT | 3 | PR | | SB |
| 36 | 50 | M | 70 | 3 | IIIB | CT | 2 | PR | | SB |
| 37 | 37 | M | 70 | 0.5 | IIIB | | 2 | PR | | SB |
| 38 | 39 | M | 70 | 8 | IIIB | S, CT | 2 | PR | | SB |
| 39 | 37 | M | 80 | 0.5 | IIIB | | 3 | PR | | SB |
| 40 | 58 | M | 90 | 0.5 | IIIA | | 3 | CR | | SB |
| 41 | 52 | M | 70 | 12 | IIIA | S, CT | 2 | PR | | SB |
| 42M | 56 | F | 70 | 6 | IIIB | S, CT | 3 | PR | | SB |
| 43 | 64 | M | 80 | 2 | IIIA | CT | 3 | CR | | SB |
| 44 | 60 | M | 70 | 0.5 | IIIB | | 2 | PR | | SB |
| 45 | 65 | M | 70 | 0.5 | IIIB | | 3 | PR | | SB |
| 46 | 47 | M | 80 | 0.25 | IVA | | 3 | CR | | SB |
| 47 | 55 | M | 90 | 2 | IIIB | CT | 2 | PR | | SB |
| 48 | 44 | M | 80 | 1.75 | IIIB | CT | 3 | CR | | SB |
| 49 | 54 | M | 60 | 8 | IVA | CT | 2 | NC | | RL |
| 50 | 66 | M | 80 | 7 | IIIB | CT | 3 | PR | | SB |
| 51 | 30 | M | 60 | 0.25 | IVA | | 3 | PR | | SB |
| 52 | 58 | M | 80 | 3 | IIIA | CT | 2 | PR | | SB |
| 53 | 48 | M | 60 | 0.75 | IIIB | | 2 | PR | | SB |
| 54 | 44 | M | 70 | 0.50 | IIIB | | 2 | PR | | SB |
| 55M | 53 | F | 80 | 13 | IIIA | CT, S | 3 | PR | | SB |
| 56 | 52 | M | 90 | 0.25 | II | | 2 | CR | | SB |
| 57M | 53 | F | 60 | 3.5 | IVA | CT | 3 | CR | | SB |
| 58 | 45 | M | 60 | 14 | IVB | CT, RT | 2 | PD | | RL, MT |
| 59 | 74 | M | 70 | 3.5 | IIIB | CT | 2 | MR | NS, I | SB |
| 60 | 38 | M | 80 | 8 | IVA | S, CT | 3 | PR | | SB |
| 61M | 72 | F | 60 | 14 | IVB | CT | 2 | NC | | MT |
| 62 | 55 | M | 70 | 3 | IIIA | CT | 2 | PR | | SB |
| 63 | 45 | M | 70 | 12 | IIIB | CT | 3 | CR | | SB |
| 64 | 60 | M | 80 | 10 | IVA | S, CT | 2 | MR | | SB |
| 65M | 49 | F | 60 | 36 | IVA | S, CT | 3 | CR | | SB |
| 66 | 63 | M | 70 | 0.75 | IIIA | | 3 | CR | | SB |
| 67M | 51 | M | 70 | 8 | IIIB | S, CT | 2 | PR | | SB |
| 68 | 59 | F | 60 | 3 | IVA | CT | 2 | PR | | SB |
| 69M | 60 | M | 80 | 0.50 | IIIA | | 2 | MR | | SB |
| 70M | 55 | M | 60 | 5 | IVA | CT, RT | 3 | PR | | SB |
| 71 | 43 | M | 80 | 0.5 | IIIA | | 2 | CR | | SB |
| 72M | 52 | M | 60 | 12 | IIIA | S, CT, RT | 2 | PR | | SB |
| 73M | 52 | F | 80 | 4 | IIIB | S, CT | 2 | PR | | SB |
| 74 | 70 | M | 60 | 0.75 | IVB | | 2 | PD | | RL, MT |

TABLE 3-continued

Patient characteristics of liver cancer

| Patient[d] | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 75 | 50 | M | 70 | 0.5 | IIIB | | 3 | PR | | SB |
| 76 | 60 | M | 80 | 12 | IVA | S, CT | 3 | PR | | SB |
| 77 | 61 | M | 60 | 25 | IVA | S, CT | 2 | NC | SGPT[+], I | RL |
| 78 | 66 | M | 70 | 0.25 | IIIB | | 2 | PR | | SB |
| 79 | 65 | M | 80 | 2 | IIIB | CT | 3 | PR | | SB |
| 80 | 61 | M | 70 | 0.50 | IIIA | | 2 | CR | | SB |
| 81 | 41 | M | 80 | 0.50 | IIIA | | 2 | PR | | SB |
| 82 | 58 | M | 80 | 0.25 | IIIB | | 2 | PR | | SB |
| 83M | 64 | M | 70 | 3 | IIIB | S, CT | 3 | CR | | SB |
| 84M | 48 | M | 60 | 4.5 | IVA | S, CT | 3 | PR | | SB |
| 85M | 62 | F | 70 | 9 | IIIB | S | 2 | PR | | SB |
| 86M | 56 | F | 60 | 0.25 | IVA | | 3 | PR | | SB |
| 87M | 65 | M | 80 | 24 | IIIB | S, CT | 2 | CR | | SB |
| 88 | 52 | M | 60 | 72 | IIIB | S, CT | 3 | PR | | SB |
| 89 | 37 | M | 70 | 0.25 | IIIA | | 2 | PR | | SB |
| 90 | 70 | M | 60 | 24 | IIIB | S, CT | 3 | PR | | SB |
| 91 | 50 | M | 80 | 0.75 | IIIA | | 2 | CR | | SB |
| 92 | 37 | M | 60 | 0.50 | IVA | | 2 | NC | | RL |
| 93 | 39 | M | 60 | 8 | IIIB | S, CT | 2 | MR | | SB |
| 94 | 37 | M | 70 | 0.25 | IIIA | | 3 | CR | | SB |
| 95M | 51 | M | 60 | 6 | IIIB | CT | 2 | PR | | SB |
| 96 | 48 | M | 80 | 2 | IIIB | CT | 3 | CR | | SB |
| 97 | 54 | M | 60 | 8 | IVA | CT | 2 | MR | | SB |
| 98M | 55 | M | 80 | 7 | IIIB | CT | 3 | CR | | SB |
| 99 | 30 | M | 70 | 0.50 | IVA | | 3 | PR | SGPT[+], I | SB |
| 100 | 61 | M | 80 | 3 | IIIA | CT | 2 | PR | | SB |
| 101 | 53 | M | 60 | 0.50 | IVA | | 3 | PR | | SB |
| 102 | 54 | M | 60 | 0.25 | IVB | | 2 | NC | | MT |
| 103 | 49 | M | 60 | 4 | IVB | S | 2 | NC | | MT |
| 104M | 42 | M | 80 | 0.75 | II | | 2 | CR | | SB |
| 105M | 53 | M | 60 | 3.5 | IVA | S, CT | 2 | PR | | SB |
| 106 | 43 | M | 80 | 1.5 | IIIA | S | 2 | CR | | SB |
| 107 | 50 | M | 70 | 0.25 | IVA | | 3 | PR | | SB |
| 108 | 64 | M | 60 | 0.75 | IVA | | 2 | MR | | SB |
| 109M | 48 | F | 80 | 0.25 | IVA | | 3 | CR | | SB |
| 110 | 43 | M | 70 | 0.50 | IVA | | 3 | CR | | SB |
| 111M | 52 | M | 60 | 2 | IVA | CT | 3 | PR | | SB |
| 112 | 56 | F | 60 | 8 | IVA | S, CT | 3 | CR | | SB |
| 113M | 65 | M | 60 | 0.25 | IVA | | 3 | CR | | SB |
| 114 | 60 | M | 70 | 5 | IVA | S, RT | 3 | CR | | SB |
| 115M | 65 | M | 80 | 8 | IIIB | CT | 2 | PR | | SB |
| 116 | 47 | M | 60 | 0.75 | IVA | | 3 | PR | | SB |
| 117 | 55 | M | 70 | 0.50 | IIIA | | 3 | CR | | SB |
| 118 | 37 | M | 60 | 0.25 | IVA | | 3 | PR | | SB |
| 119 | 57 | M | 70 | 0.25 | IIIB | | 3 | CR | | SB |
| 120 | 60 | M | 80 | 0.25 | IVA | | 2 | MR | | SB |
| 121M | 68 | M | 60 | 2 | IVB | CT | 2 | PD | | RL, MT |
| 122 | 65 | M | 70 | 0.5 | IVA | | 3 | PR | | SB |
| 123 | 44 | F | 60 | 0.25 | IVA | | 2 | MR | | SB |
| 124 | 49 | M | 60 | 5 | IVA | CT | 2 | NC | | SB |
| 125 | 54 | M | 60 | 0.50 | IVA | | 3 | CR | | SB |
| 126 | 45 | M | 70 | 0.25 | IVA | | 3 | PR | | SB |
| 127M | 55 | M | 60 | 0.50 | IVA | | 3 | PR | | SB |
| 128 | 52 | M | 80 | 0.25 | IVA | | 2 | MR | | SB |
| 129M | 40 | M | 60 | 4 | IIIB | CT | 3 | PR | | SB |
| 130 | 61 | M | 60 | 0.75 | IVA | | 2 | MR | | SB |
| 131 | 49 | M | 70 | 3 | IIIB | CT | 3 | PR | | SB |
| 132 | 66 | M | 60 | 0.25 | IVA | | 3 | PR | | SB |
| 133M | 53 | F | 60 | 0.25 | IIIA | | 2 | CR | | SB |
| 134 | 51 | M | 60 | 12 | IIIB | CT | 2 | PR | | SB |
| 135 | 52 | M | 80 | 0.25 | IIIB | | 3 | CR | | SB |

[a]Interval between diagnosis of primary tumor and start of CHML treatment.
[b]Follow up since the trial start.
[c]PS, performance status (Karnofsky); S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT[+], glutamic-pyruvic transaminase increase; NS, nausea.
[d]No mark M, hepatocellular carcinoma;
[d]mark M, metastatic cancer to the liver.

TABLE 4

Patient characteristics of lung cancer

| Patient[d] | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 1 | 68 | F | 70 | 4 | IV | CT | 2 | MR | | RL, MT |
| 2 | 62 | F | 80 | 0.5 | IIB | | 3 | CR | | SB |
| 3 | 48 | M | 60 | 4 | IV | CT | 2 | PD | | RL, MT |
| 4 | 43 | F | 60 | 5 | IV | CT | 2 | PD | | RL, MT |
| 5 | 54 | F | 70 | 4 | IV | CT | 2 | NC | | RL, MT |
| 6 | 40 | F | 70 | 3 | IIIB | RT | 2 | MR | | MT |
| 7 | 55 | F | 70 | 0.5 | IIB | | 3 | PR | | SB |
| 8 | 65 | F | 80 | 0.25 | IIB | | 3 | CR | | SB |
| 9 | 62 | M | 80 | 7 | IIA | S, RT | 3 | CR | | SB |
| 10S | 50 | M | 80 | 10 | IIB | S, CT, RT | 3 | CR | | SB |
| 11 | 40 | M | 70 | 5 | IIB | S, RT | 3 | CR | | SB |
| 12 | 48 | M | 70 | 5 | IV | CT | 2 | NC | | RL, MT |
| 13 | 60 | M | 70 | 3 | IIA | RT | 3 | PR | | SB |
| 14 | 46 | F | 70 | 0.5 | IIIA | | 3 | CR | | SB |
| 15 | 64 | M | 80 | 3 | IIIA | RT | 3 | CR | | SB |
| 16 | 49 | M | 70 | 4 | IIB | RT | 3 | PR | | SB |
| 17 | 40 | F | 80 | 3 | IIB | RT | 3 | PR | | SB |
| 18 | 52 | F | 70 | 10 | IIIB | CT, RT | 2 | NC | | RL |
| 19 | 64 | M | 60 | 4 | IV | CT | 2 | PD | SGPT+, I | RL, MT |
| 20 | 59 | F | 70 | 5 | IV | CT | 2 | NC | | MT |
| 21 | 75 | F | 70 | 3 | IIB | RT | 3 | PR | | SB |
| 22S | 60 | F | 80 | 24 | IIB | S, CT, RT | 3 | CR | | SB |
| 23 | 61 | M | 80 | 0.5 | IIIA | | 3 | PR | | RL |
| 24 | 53 | M | 70 | 9 | IIIA | CT, RT | 3 | PR | | SB |
| 25 | 80 | M | 70 | 36 | IIA | S, CT, RT | 3 | CR | | SB |
| 26 | 41 | F | 80 | 12 | IIIA | S, CT, RT | 3 | PR | | SB |
| 27 | 62 | M | 70 | 9 | IIIA | CT, RT | 3 | PR | | SB |
| 28 | 62 | M | 60 | 12 | IIIB | CT, RT | 2 | MR | | SB |
| 29S | 67 | M | 70 | 3 | IIIA | RT | 3 | CR | | SB |
| 30 | 42 | M | 80 | 3 | IIIA | RT | 3 | PR | | SB |
| 31 | 62 | F | 80 | 3.5 | IIIA | RT | 3 | PR | | SB |
| 32 | 72 | M | 70 | 4 | IIB | CT, RT | 2 | PR | | SB |
| 33 | 68 | F | 60 | 0.5 | IV | | 2 | MR | | RL, MT |
| 34 | 62 | F | 70 | 0.25 | IIA | | 3 | CR | | SB |
| 35 | 48 | F | 60 | 4 | IV | CT, RT | 2 | PD | | RL, MT |
| 36 | 54 | F | 60 | 2.5 | IV | RT | 3 | NC | | MT |
| 37 | 62 | M | 70 | 10 | IIA | S, CT, RT | 2 | PR | | SB |
| 38 | 55 | F | 80 | 0.50 | IIA | | 3 | CR | | SB |
| 39 | 40 | F | 60 | 3 | IIB | RT | 3 | CR | | SB |
| 40 | 75 | F | 70 | 5 | IIIA | S, RT | 3 | PR | | SB |
| 41 | 52 | F | 80 | 0.25 | IIB | | 3 | CR | | SB |
| 42 | 63 | F | 80 | 5 | IIA | S, RT | 3 | CR | | SB |
| 43 | 75 | M | 60 | 2.5 | IIIA | CT | 2 | NC | NS, I | RL, MT |
| 44 | 53 | M | 60 | 3 | IIIB | RT | 3 | MR | | SB |
| 45 | 61 | M | 80 | 0.75 | IIA | | 3 | CR | | SB |
| 46 | 82 | M | 70 | 2.5 | IIB | RT | 3 | CR | | SB |
| 47 | 64 | M | 80 | 2.5 | IIB | RT | 3 | PR | | SB |
| 48 | 60 | M | 60 | 3 | IIIB | RT | 3 | MR | | SB |
| 49 | 44 | M | 60 | 5 | IIIB | CT, RT | 2 | MR | | SB |
| 50 | 64 | M | 70 | 4 | IIA | RT | 2 | PR | | SB |
| 51S | 66 | M | 60 | 8 | IIIB | CT, RT | 3 | CR | | SB |
| 52 | 52 | M | 60 | 2.5 | IIA | RT | 2 | PR | | SB |
| 53S | 51 | F | 60 | 2.5 | IIIA | RT | 3 | PR | | SB |
| 54 | 62 | M | 70 | 8 | IIA | S, CT, RT | 2 | PR | | SB |
| 55 | 34 | F | 60 | 4 | IIIA | S, CT, RT | 3 | MR | | SB |
| 56 | 73 | M | 70 | 3 | IIA | RT | 2 | PR | | SB |
| 57S | 58 | M | 60 | 4 | IIIA | S, RT | 3 | PR | | SB |
| 58 | 51 | M | 60 | 10 | IIA | S, RT | 3 | CR | | SB |
| 59 | 45 | M | 70 | 3 | IIA | CT | 2 | PR | | SB |
| 60 | 42 | M | 80 | 3 | IIIA | RT | 3 | PR | | SB |
| 61 | 59 | M | 60 | 4 | IIIB | RT | 3 | MR | | SB |
| 62 | 40 | M | 60 | 14 | IV | S, CT | 2 | NC | | RL, MT |
| 63 | 61 | M | 70 | 5 | IIB | CT, RT | 2 | CR | | SB |
| 64 | 46 | F | 70 | 2.5 | IIIA | RT | 3 | PR | | SB |
| 65S | 61 | F | 60 | 3 | IIIA | RT | 3 | PR | | SB |
| 66 | 64 | M | 60 | 2.5 | IIB | CT | 2 | PR | | SB |
| 67 | 56 | F | 60 | 2.5 | IV | CT | 2 | PD | | RL, MT |
| 68 | 77 | F | 70 | 3 | IIIA | RT | 2 | CR | | SB |
| 69 | 46 | F | 60 | 4 | IIIB | CT | 2 | NC | | RL |
| 70 | 75 | M | 70 | 5 | IIA | CT | 2 | PR | | SB |
| 71 | 63 | M | 60 | 0.75 | IV | | 2 | PD | | RL, MT |
| 72S | 52 | M | 70 | 2.5 | IIIB | RT | 3 | CR | | SB |
| 73 | 52 | F | 60 | 10 | IIIB | S, CT, RT | 2 | MR | | SB |
| 74 | 40 | F | 70 | 0.50 | IIA | | 3 | PR | | SB |

TABLE 4-continued

Patient characteristics of lung cancer

| Patient[d] | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 75 | 65 | M | 60 | 2.5 | IIIB | RT | 3 | PR | | SB |
| 76 | 51 | F | 70 | 8 | IIA | CT, RT | 2 | PR | | SB |
| 77 | 58 | M | 60 | 12 | IV | S, CT, RT | 2 | NC | | RL, MT |
| 78 | 56 | F | 60 | 0.75 | IIIB | | 2 | NC | | SB |
| 79 | 63 | M | 60 | 3 | IIIA | RT | 3 | PR | | SB |
| 80 | 56 | F | 70 | 2.5 | IIA | RT | 3 | CR | | SB |
| 81 | 42 | F | 60 | 2.5 | IIIA | RT | 2 | PR | | SB |
| 82 | 54 | F | 60 | 5 | IIIA | CT, RT | 3 | PR | | SB |
| 83 | 48 | M | 60 | 4 | IIIB | S, CT | 3 | MR | | SB |
| 84 | 62 | F | 60 | 3 | IIB | RT | 2 | PR | | SB |
| 85 | 68 | F | 60 | 3.5 | IIIB | CT, RT | 2 | NC | | SB |
| 86 | 64 | M | 70 | 2.5 | IIIA | RT | 3 | MR | | SB |
| 87S | 47 | F | 60 | 5 | IIIA | CT, RT | 2 | PR | | SB |
| 88 | 60 | M | 60 | 3.5 | IIIA | RT | 3 | PR | | SB |
| 89 | 40 | M | 70 | 0.50 | IIA | | 3 | CR | | SB |
| 90 | 50 | F | 70 | 0.50 | IIA | | 3 | PR | | SB |
| 91 | 65 | M | 70 | 7 | IIB | CT, RT | 3 | PR | | SB |
| 92 | 50 | F | 70 | 23 | IIA | S, CT, RT | 3 | CR | | SB |
| 93 | 43 | F | 60 | 12 | IIIA | S, CT, RT | 3 | PR | | SB |
| 94S | 57 | M | 60 | 3 | IIIB | RT | 3 | MR | | SB |
| 95 | 33 | M | 60 | 6 | IIIB | CT, RT | 2 | MR | SGPT[+], I | RL |
| 96 | 42 | M | 70 | 24 | IIA | S, CT, RT | 3 | CR | | SB |
| 97 | 70 | M | 60 | 10 | IIIB | S, CT, RT | 3 | PR | | SB |
| 98 | 55 | F | 60 | 15 | IV | CT | 2 | PD | | RL, MT |
| 99 | 35 | F | 60 | 2.5 | IV | RT | 3 | PR | | SB |
| 100 | 56 | M | 70 | 0.50 | IIB | | 3 | CR | | SB |
| 101 | 57 | M | 80 | 0.75 | IIA | | 3 | PR | | SB |
| 102 | 52 | F | 60 | 15 | IIIB | S, CT, RT | 3 | MR | | SB |

[a]Interval between diagnosis of primary tumor and start of CHML treatment.
[b]Follow up since the trial start.
[c]PS, performance status (Kamofsky); S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT[+], glutamic-pyruvic transaminase increase; NS, nausea.
[d]No mark S, non-small cell lung cancer;
[d]mark S, small cell lung cancer.

TABLE 5

Patient characteristics of skin cancer

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 1 | 43 | M | 90 | 0.25 | II | | 2 | CR | | SB |
| 2 | 79 | M | 70 | 0.25 | II | | 2 | CR | | SB |
| 3 | 72 | M | 90 | 0.25 | III | | 2 | PR | | SB |
| 4 | 68 | M | 90 | 0.25 | II | | 3 | CR | | SB |
| 5 | 67 | F | 90 | 0.25 | III | | 3 | CR | | SB |
| 6 | 46 | M | 80 | 0.25 | III | | 2 | CR | | SB |
| 7 | 23 | M | 80 | 3 | IV | S, RT | 2 | MR | | MT |
| 8 | 63 | F | 80 | 0.25 | III | | 2 | CR | | SB |
| 9 | 60 | M | 90 | 0.25 | III | | 2 | CR | | SB |
| 10 | 81 | M | 70 | 0.25 | II | | 2 | CR | | SB |
| 11 | 43 | M | 90 | 0.25 | II | | 2 | CR | | SB |
| 12 | 47 | M | 90 | 0.25 | II | | 2 | PR | | SB |
| 13 | 54 | M | 90 | 0.25 | III | | 2 | CR | | SB |
| 14 | 76 | M | 80 | 0.25 | II | | 2 | PR | | SB |
| 15 | 58 | M | 80 | 0.25 | II | | 2 | PR | | SB |
| 16 | 62 | M | 90 | 0.25 | II | | 2 | CR | | SB |
| 17 | 71 | M | 70 | 0.25 | II | | 2 | CR | | SB |
| 18 | 21 | F | 90 | 0.25 | III | | 2 | PR | | SB |
| 19 | 41 | M | 90 | 0.25 | II | | 2 | CR | | SB |
| 20 | 38 | F | 80 | 3.25 | III | S, RT | 2 | PR | | SB |
| 21 | 60 | M | 80 | 0.25 | II | | 2 | CR | | SB |
| 22 | 56 | M | 90 | 0.25 | II | | 2 | CR | | SB |
| 23 | 62 | M | 90 | 0.75 | II | | 2 | CR | | SB |
| 24 | 41 | M | 90 | 0.25 | II | | 2 | CR | | SB |
| 25 | 22 | M | 90 | 0.25 | III | | 2 | CR | | SB |
| 26 | 48 | M | 90 | 0.50 | II | | 2 | CR | | SB |
| 27 | 53 | M | 90 | 0.50 | III | | 2 | PR | | SB |
| 28 | 41 | F | 80 | 0.25 | III | | 3 | CR | | SB |
| 29 | 70 | M | 90 | 0.25 | III | | 2 | CR | | SB |

TABLE 5-continued

Patient characteristics of skin cancer

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 30 | 63 | F | 60 | 0.25 | IV | | 2 | PR | | MT |
| 31 | 59 | M | 90 | 0.25 | II | | 2 | CR | | SB |
| 32 | 21 | M | 90 | 0.25 | III | | 2 | CR | | SB |
| 33 | 28 | M | 90 | 0.25 | III | | 2 | CR | | SB |
| 34 | 42 | M | 90 | 0.25 | II | | 2 | CR | | SB |
| 35 | 50 | M | 90 | 0.50 | III | | 2 | PR | | SB |
| 36 | 25 | M | 90 | 0.25 | II | | 2 | CR | | SB |
| 37 | 42 | M | 90 | 0.50 | II | | 2 | CR | | SB |
| 38 | 56 | M | 90 | 0.25 | II | | 2 | CR | | SB |
| 39 | 61 | M | 80 | 0.25 | III | | 2 | PR | | SB |
| 40 | 35 | F | 90 | 0.25 | III | | 2 | CR | | SB |
| 41 | 57 | M | 90 | 0.25 | II | | 2 | CR | | SB |
| 42 | 72 | F | 60 | 3 | IV | S, RT | 2 | MR | | MT |
| 43 | 67 | M | 90 | 0.25 | II | | 2 | CR | | SB |
| 44 | 44 | M | 90 | 0.25 | II | | 2 | CR | | SB |
| 45 | 27 | F | 90 | 0.25 | II | | 2 | CR | | SB |
| 46 | 35 | M | 90 | 0.25 | II | | 2 | CR | | SB |
| 47 | 37 | M | 90 | 0.25 | III | | 2 | PR | | SB |
| 48 | 48 | M | 90 | 0.25 | II | | 2 | CR | | SB |
| 49 | 30 | M | 80 | 0.25 | III | | 2 | CR | | SB |
| 50 | 25 | F | 90 | 0.25 | III | | 2 | PR | | SB |
| 51 | 60 | M | 80 | 0.50 | III | | 2 | PR | | SB |
| 52 | 77 | F | 60 | 5 | IV | S, RT | 2 | MR | | MT |
| 53 | 42 | M | 90 | 0.25 | II | | 2 | CR | | SB |
| 54 | 45 | M | 80 | 0.25 | III | | 2 | PR | | SB |
| 55 | 63 | M | 90 | 0.25 | III | | 2 | CR | | SB |
| 56 | 38 | M | 90 | 0.25 | II | | 2 | CR | | SB |
| 57 | 32 | M | 80 | 0.50 | III | | 2 | PR | | SB |
| 58 | 29 | M | 100 | 0.25 | II | | 2 | CR | | SB |
| 59 | 41 | M | 90 | 0.25 | III | | 2 | PR | | SB |
| 60 | 70 | M | 90 | 0.25 | II | | 2 | CR | | SB |
| 61 | 51 | M | 90 | 0.25 | III | | 2 | PR | | SB |
| 62 | 61 | M | 80 | 0.25 | III | | 2 | PR | | SB |
| 63 | 53 | M | 70 | 0.25 | IV | | 2 | MR | | MT |
| 64 | 40 | M | 90 | 0.50 | II | | 2 | CR | | SB |
| 65 | 55 | M | 90 | 0.25 | II | | 2 | CR | | SB |
| 66 | 47 | M | 90 | 0.25 | III | | 2 | PR | | SB |
| 67 | 39 | M | 90 | 0.25 | II | | 2 | CR | | SB |

[a]Interval between diagnosis of primary tumor and start of CHML treatment.
[b]Follow up since the trial start.
[c]PS, performance status (Karnofsky); S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT↑, glutamic-pyruvic transaminase increase; NS, nausea.

TABLE 6

Patient characteristics of breast cancer

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 1 | 37 | F | 90 | 8 | IIIA | S, CT | 3 | CR | | SB |
| 2 | 46 | F | 90 | 12 | IIIB | S, CT | 3 | CR | | SB |
| 3 | 61 | F | 80 | 8 | IV | S, CT | 3 | PR | | MT |
| 4 | 52 | F | 90 | 38 | IIIA | S, CT | 3 | CR | | SB |
| 5 | 55 | F | 70 | 11 | IIB | S, CT | 2 | PR | | SB |
| 6 | 43 | F | 60 | 8 | IIIB | S, CT | 2 | MR | | RL |
| 7 | 43 | F | 70 | 8 | IIIA | S, CT | 2 | PR | | SB |
| 8 | 53 | F | 60 | 9 | IV | S, CT | 2 | NC | | MT |
| 9 | 68 | F | 60 | 0.5 | IIA | | 2 | PR | | SB |
| 10 | 45 | F | 70 | 10 | IV | S, CT | 2 | PD | | RL, MT |
| 11 | 42 | F | 80 | 12 | IIIB | S, CT | 3 | CR | | SB |
| 12 | 68 | F | 90 | 3.5 | IIIA | S, RT | 3 | PR | | SB |
| 13 | 43 | F | 70 | 3.5 | IIB | S, RT | 2 | PR | | SB |
| 14 | 44 | F | 80 | 14 | IIIB | S, CT | 3 | PR | | SB |
| 15 | 34 | F | 60 | 9 | IV | S, CT | 2 | NC | | MT |
| 16 | 61 | F | 60 | 10 | IV | S, CT | 2 | MR | | RL, MT |
| 17 | 54 | F | 70 | 12 | IIIA | S, CT | 3 | PR | | SB |
| 18 | 56 | F | 80 | 10 | IIB | S, CT | 3 | CR | | SB |
| 19 | 41 | F | 70 | 3.5 | IIIA | S, RT | 3 | PR | | SB |
| 20 | 68 | F | 70 | 8 | IIB | S, CT | 2 | CR | | SB |
| 21 | 23 | F | 60 | 9 | IIIB | S, CT | 2 | CR | | SB |

TABLE 6-continued

Patient characteristics of breast cancer

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 22 | 46 | F | 70 | 4 | IV | S, CT | 3 | PR | | MT |
| 23 | 42 | F | 80 | 5 | IIIA | S, CT | 3 | CR | | SB |
| 24 | 69 | F | 60 | 11 | IIIB | S, CT, RT | 3 | PR | | SB |
| 25 | 52 | F | 70 | 14 | IIB | S, CT, RT | 2 | CR | | SB |
| 26 | 62 | F | 60 | 16 | IIIA | S, CT | 2 | CR | | SB |
| 27 | 43 | F | 60 | 8 | IV | S, CT | 3 | PR | | MT |
| 28 | 44 | F | 70 | 6 | IV | S, CT | 2 | PD | | RL, MT |
| 29 | 53 | F | 70 | 11 | IIIA | S, CT | 2 | CR | | SB |
| 30 | 34 | F | 60 | 6 | IIIA | S, CT | 3 | CR | | SB |
| 31 | 71 | F | 70 | 5 | IIIA | S, CT | 2 | CR | | SB |
| 32 | 28 | F | 70 | 10 | IIIB | S, RT | 2 | PR | | SB |
| 33 | 61 | F | 70 | 15 | IIIB | S, CT, RT | 3 | PR | | SB |
| 34 | 48 | F | 60 | 3 | IV | S, CT | 2 | MR | SGPT[+], I | MT |
| 35 | 41 | F | 70 | 9 | IIIB | S, CT | 2 | CR | | SB |
| 36 | 51 | F | 70 | 3 | IIA | S, CT | 2 | CR | | SB |
| 37 | 70 | F | 60 | 23 | IIIA | S, CT, RT | 3 | CR | | SB |
| 38 | 45 | F | 70 | 6 | IIIA | S, RT | 3 | CR | | SB |
| 39 | 32 | F | 70 | 0.75 | IIIA | | 3 | CR | | SB |
| 40 | 45 | F | 80 | 26 | IIIA | S, CT | 2 | CR | | SB |
| 41 | 51 | F | 70 | 50 | IIIA | S, CT | 2 | CR | | SB |
| 42 | 46 | F | 70 | 10 | IIB | S, CT | 2 | CR | | SB |
| 43 | 42 | F | 70 | 5 | IIIA | S, CT | 3 | CR | | SB |
| 44 | 37 | F | 80 | 7 | IIB | S | 3 | PR | | SB |
| 45 | 43 | F | 70 | 8 | IIB | S, CT | 2 | CR | | SB |
| 46 | 46 | F | 60 | 16 | IIIA | S, CT | 2 | PR | | SB |
| 47 | 32 | F | 70 | 7 | IV | S, CT | 3 | PR | | MT |
| 48 | 42 | F | 80 | 16 | IIB | S, CT | 2 | CR | | SB |
| 49 | 43 | F | 70 | 15 | IIIA | S, CT | 2 | CR | | SB |
| 50 | 51 | F | 70 | 10 | IV | S, CT | 2 | MR | | MT |
| 51 | 53 | F | 60 | 5 | IIIB | S, CT | 2 | PR | | SB |
| 52 | 28 | F | 70 | 36 | IIIB | S, RT | 3 | PR | | SB |
| 53 | 67 | F | 60 | 6 | IIIB | S, CT | 2 | PR | | SB |
| 54 | 62 | F | 60 | 3 | IV | S, CT | 2 | PR | | MT |
| 55 | 52 | F | 70 | 15 | IIA | S, CT | 2 | CR | | SB |
| 56 | 39 | F | 60 | 3 | IV | S, CT | 2 | NC | | MT |
| 57 | 32 | F | 70 | 0.50 | IIA | | 3 | CR | | SB |
| 58 | 43 | F | 70 | 7 | IIIA | S, RT | 3 | CR | | SB |
| 59 | 55 | F | 60 | 0.75 | IV | | 2 | PR | | MT |
| 60 | 36 | F | 70 | 9 | IIB | S, CT | 2 | CR | | SB |
| 61 | 49 | F | 60 | 5 | IV | S, CT | 2 | NC | | RL, MT |
| 62 | 62 | F | 60 | 7 | IIIA | S, CT | 2 | CR | | SB |
| 63 | 31 | F | 80 | 6 | IIIB | S, CT | 3 | PR | | SB |
| 64 | 35 | F | 60 | 18 | IV | S, CT, RT | 2 | MR | | MT |
| 65 | 34 | F | 60 | 3 | IV | S, CT | 2 | PR | | MT |

[a]Interval between diagnosis of primary tumor and start of CHML treatment.
[b]Follow up since the trial start.
[c]PS, performance status (Karnofsky); S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT[+], glutamic-pyruvic transaminase increase; NS, nausea.

TABLE 7

Patient characteristics of brain glioma

| Patient | Age | Sex | PS[c] | Interval[a] (months) | Clinical stage[19] | Previous treatment | No. of cycles | Response | Toxicity grade | Follow up[b] (6 months) |
|---|---|---|---|---|---|---|---|---|---|---|
| 1 | 18 | M | 100 | 16 | II | S, CT, RT | 3 | CR | | SB |
| 2 | 37 | F | 90 | 5 | II | S, RT | 3 | CR | | SB |
| 3 | 68 | M | 80 | 0.75 | IV | S | 2 | NC | | RL |
| 4 | 34 | M | 90 | 9 | II | S, CT, RT | 3 | CR | | SB |
| 5 | 46 | M | 70 | 3 | II | S, RT | 3 | PR | SGPT[+], I | SB |
| 6 | 72 | M | 60 | 3 | IV | S, RT | 2 | MR | | RL |
| 7 | 76 | M | 60 | 12 | II | S, CT, RT | 2 | MR | | SB |
| 8 | 34 | F | 70 | 0.75 | III | S | 3 | PR | | SB |
| 9 | 66 | M | 70 | 0.75 | IV | S | 2 | PR | | SB |
| 10 | 45 | F | 60 | 25 | II | S, CT, RT | 3 | PR | | SB |
| 11 | 14 | F | 90 | 84 | II | S, CT, RT | 3 | CR | | SB |
| 12 | 59 | F | 90 | 12 | II | S, CT, RT | 3 | CR | | SB |
| 13 | 46 | F | 70 | 3.5 | III | S, RT | 3 | PR | | SB |
| 14 | 63 | M | 60 | 10 | II | S, CT, RT | 2 | MR | | SB |
| 15 | 72 | M | 80 | 3 | II | S, RT | 2 | PR | | SB |

TABLE 7-continued

Patient characteristics of brain glioma

| Patient | Age | Sex | PS[c] | Interval[a] (months) | Clinical stage[19] | Previous treatment | No. of cycles | Response | Toxicity grade | Follow up[b] (6 months) |
|---|---|---|---|---|---|---|---|---|---|---|
| 16 | 20 | M | 90 | 10 | II | S, CT, RT | 3 | CR | | SB |
| 17 | 65 | M | 80 | 0.5 | II | S | 2 | PR | | SB |
| 18 | 50 | M | 70 | 3 | IV | S, RT | 2 | NC | | RL |
| 19 | 44 | M | 90 | 10 | II | S, CT, RT | 2 | PR | | SB |
| 20 | 21 | M | 80 | 3 | II | S, RT | 2 | PR | | SB |
| 21 | 29 | F | 90 | 0.75 | IV | S | 3 | PR | | SB |
| 22 | 18 | M | 90 | 0.75 | III | S | 3 | PR | | SB |
| 23 | 38 | M | 90 | 0.75 | II | S | 2 | PR | | SB |
| 24 | 28 | F | 80 | 0.75 | III | S | 2 | MR | | SB |
| 25 | 29 | F | 70 | 0.25 | IV | S | 3 | MR | | SB |
| 26 | 28 | F | 90 | 58 | II | S, CT | 2 | CR | | SB |
| 27 | 45 | M | 60 | 4 | IV | S, RT | 3 | CR | | SB |
| 28 | 31 | M | 80 | 1 | II | S | 2 | CR | | SB |
| 29 | 32 | M | 70 | 8 | II | S | 2 | PR | | SB |
| 30 | 17 | M | 60 | 0.75 | II | S | 2 | PR | | SB |
| 31 | 18 | M | 60 | 3 | III | S, RT | 2 | CR | | SB |
| 32 | 38 | M | 70 | 0.5 | III | S | 2 | MR | NS, I | RL |
| 33 | 61 | M | 60 | 0.75 | IV | S | 2 | MR | | RL |
| 34 | 18 | M | 60 | 18 | III | S, CT, RT | 3 | CR | | SB |
| 35 | 37 | F | 70 | 4 | III | S, RT | 3 | CR | | SB |
| 36 | 34 | M | 60 | 7 | IV | S, CT, RT | 3 | PR | | SB |
| 37 | 34 | F | 60 | 3 | III | S, RT | 3 | PR | | SB |
| 38 | 13 | F | 80 | 120 | II | S, CT, RT | 2 | PR | | SB |
| 39 | 63 | M | 70 | 5 | III | S, RT | 3 | PR | | SB |
| 40 | 35 | F | 70 | 7 | II | S, CT, RT | 2 | CR | | SB |
| 41 | 50 | M | 60 | 24 | IV | S, CT | 2 | NC | | RL |
| 42 | 48 | M | 60 | 3 | II | S, RT | 2 | PR | | SB |
| 43 | 50 | M | 60 | 5 | IV | S, CT | 2 | NC | | RL |
| 44 | 10 | M | 60 | 2.5 | IV | S, RT | 2 | PR | | SB |
| 45 | 15 | F | 70 | 5 | III | S, RT | 3 | PR | | SB |
| 46 | 62 | M | 70 | 0.5 | II | S | 2 | CR | | SB |
| 47 | 66 | M | 60 | 2.5 | III | S, RT | 3 | CR | | SB |
| 48 | 74 | M | 60 | 8 | III | S, RT | 3 | PR | | SB |
| 49 | 46 | M | 70 | 3 | III | S, RT | 2 | PR | | SB |
| 50 | 53 | F | 70 | 14 | II | S, CT | 2 | CR | | SB |
| 51 | 68 | M | 60 | 35 | II | S, CT, RT | 2 | CR | | SB |
| 52 | 69 | F | 60 | 7 | II | S, RT | 2 | CR | | SB |
| 53 | 46 | F | 70 | 10 | III | S, CT, RT | 2 | MR | | SB |
| 54 | 60 | M | 60 | 10 | III | S, CT, RT | 3 | PR | | SB |
| 55 | 47 | F | 70 | 6 | II | S, RT | 2 | CR | | SB |
| 56 | 32 | M | 70 | 0.5 | III | S | 3 | PR | | SB |
| 57 | 45 | M | 60 | 2.5 | IV | S, RT | 3 | PR | | SB |
| 58 | 33 | M | 70 | 2.5 | III | S, RT | 3 | CR | | SB |
| 59 | 48 | F | 90 | 8 | II | S, CT | 2 | PR | | SB |
| 60 | 20 | M | 60 | 6 | III | S, CT, RT | 2 | PR | | SB |
| 61 | 47 | M | 70 | 1 | II | S | 2 | CR | | SB |
| 62 | 56 | M | 60 | 3 | IV | S, CT | 3 | NC | | RL |
| 63 | 22 | M | 60 | 0.5 | II | S | 3 | CR | | SB |
| 64 | 65 | M | 60 | 2.5 | III | S, RT | 3 | CR | | SB |
| 65 | 50 | M | 70 | 0.5 | III | S | 2 | MR | | SB |

[a]Interval between diagnosis of primary tumor and start of CHML treatment.
[b]Follow up since the trial start.
[c]PS, performance status (Karnofsky); S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT[+], glutamic-pyruvic transaminase increase; NS, nausea.

TABLE 8

Patient characteristics of colon and rectum cancer

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 1 | 46 | M | 60 | 14 | II | S, CT | 3 | PR | | SB |
| 2 | 81 | F | 60 | 4.5 | II | S, CT | 3 | CR | | SB |
| 3 | 66 | F | 70 | 4 | IV | S, CT | 2 | NC | | RL, MT |
| 4 | 55 | M | 60 | 36 | II | S, CT | 3 | CR | | SB |
| 5 | 51 | M | 60 | 14 | II | S, CT | 2 | PR | SGPT[+], I | SB |
| 6 | 74 | F | 70 | 15 | III | S, CT | 3 | PR | | SB |
| 7 | 46 | M | 70 | 12 | II | S, CT | 3 | CR | | SB |
| 8 | 66 | F | 60 | 20 | III | S, CT | 2 | PR | | SB |
| 9 | 55 | F | 70 | 0.25 | II | | 2 | CR | | SB |

TABLE 8-continued

Patient characteristics of colon and rectum cancer

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 10 | 80 | F | 60 | 0.25 | III | | 2 | PR | | SB |
| 11 | 58 | M | 60 | 16 | III | S, CT | 2 | PR | | SB |
| 12 | 60 | M | 60 | 1 | IV | S | 2 | PD | | RL, MT |
| 13 | 51 | F | 60 | 14 | III | S, CT | 2 | MR | | SB |
| 14 | 54 | M | 80 | 13 | III | S, CT | 3 | PR | | SB |
| 15 | 33 | M | 70 | 21 | III | S, CT, RT | 3 | CR | | SB |
| 16 | 70 | F | 70 | 0.25 | II | | 2 | PR | | SB |
| 17 | 48 | M | 60 | 1 | III | S | 2 | MR | | SB |
| 18 | 57 | M | 60 | 0.25 | III | | 3 | PR | | SB |
| 19 | 60 | M | 70 | 12 | III | S, CT | 2 | MR | | SB |
| 20 | 63 | F | 60 | 6 | II | S, CT | 2 | PR | | SB |
| 21 | 62 | F | 70 | 6 | IV | S, CT | 2 | NC | | MT |
| 22 | 47 | M | 70 | 14 | II | S, CT | 2 | PR | | SB |
| 23 | 66 | F | 70 | 22 | III | S, CT | 2 | PR | | SB |
| 24 | 56 | F | 80 | 0.5 | III | | 3 | CR | | SB |
| 25 | 81 | F | 60 | 4 | IV | S, CT | 2 | MR | | MT |
| 26 | 59 | M | 60 | 12 | IV | S, CT | 2 | MR | | MT |
| 27 | 61 | M | 90 | 14 | II | S, CT | 2 | PR | | SB |
| 28 | 51 | M | 80 | 9 | III | S, CT | 3 | CR | | SB |
| 29 | 44 | M | 60 | 14 | IV | S, CT | 2 | MR | | MT |
| 30 | 34 | M | 60 | 22 | IV | S, CT | 3 | PR | | MT |
| 31 | 20 | F | 70 | 32 | III | S, CT | 2 | PR | | SB |
| 32 | 61 | M | 60 | 30 | III | S, CT | 3 | CR | | SB |
| 33 | 46 | F | 60 | 16 | III | S, CT | 3 | PR | | SB |
| 34 | 43 | M | 60 | 12 | IV | S, CT | 2 | NC | | MT |
| 35 | 55 | M | 70 | 12 | III | S, CT | 3 | PR | | SB |
| 36 | 75 | F | 60 | 0.5 | III | | 3 | CR | | SB |
| 37 | 52 | M | 80 | 0.25 | III | | 2 | PR | | SB |
| 38 | 74 | F | 70 | 0.25 | II | | 2 | CR | | SB |
| 39 | 57 | F | 70 | 0.5 | III | | 3 | CR | | SB |
| 40 | 68 | M | 80 | 0.25 | II | | 2 | CR | | SB |
| 41 | 42 | M | 80 | 1.5 | III | S | 3 | PR | | SB |
| 42 | 31 | F | 90 | 0.25 | II | | 2 | CR | | SB |
| 43 | 53 | M | 60 | 0.25 | IV | | 3 | PR | | MT |
| 44 | 45 | F | 70 | 0.5 | III | | 2 | PR | SGPT+, I | SB |
| 45 | 26 | M | 60 | 8 | III | S, CT | 2 | PR | | SB |
| 46 | 35 | F | 70 | 0.25 | II | | 2 | CR | | SB |
| 47 | 38 | M | 60 | 7 | IV | S, CT | 2 | NC | | MT |
| 48 | 57 | F | 60 | 0.25 | III | | 2 | PR | | SB |
| 49 | 35 | M | 70 | 0.5 | III | | 2 | MR | | SB |
| 50 | 50 | M | 80 | 0.25 | II | | 2 | CR | | SB |
| 51 | 36 | F | 70 | 0.5 | III | | 2 | PR | | SB |
| 52 | 29 | M | 70 | 0.25 | III | | 3 | CR | | SB |
| 53 | 38 | M | 70 | 0.25 | III | | 3 | CR | | SB |
| 54 | 33 | F | 60 | 3 | III | S, CT | 2 | PR | | SB |
| 55 | 36 | F | 90 | 0.25 | II | | 2 | CR | | SB |
| 56 | 60 | M | 60 | 120 | III | S, CT | 3 | PR | | SB |
| 57 | 67 | F | 80 | 0.25 | III | | 3 | CR | | SB |
| 58 | 51 | F | 60 | 24 | IV | S, CT | 3 | PR | | MT |
| 59 | 47 | M | 60 | 0.25 | IV | | 3 | PR | NS, I | MT |
| 60 | 65 | M | 70 | 10 | III | S, CT | 2 | PR | | SB |
| 61 | 48 | F | 80 | 6 | III | S, CT | 3 | CR | | SB |

[a]Interval between diagnosis of primary tumor and start of CHML treatment.
[b]Follow up since the trial start.
[c]PS, performance status (Karnofsky); S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT+, glutamic-pyruvic transaminase increase; NS, nausea.

TABLE 9

Patient characteristics of stomach cancer

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 1 | 47 | M | 70 | 0.5 | II | | 3 | PR | | SB |
| 2 | 56 | M | 60 | 4 | IV | S, CT | 2 | MR | | MT |
| 3 | 40 | M | 60 | 0.5 | IV | | 2 | MR | | MT |
| 4 | 46 | F | 70 | 14 | IIIA | S, CT | 3 | PR | | SB |
| 5 | 51 | M | 70 | 0.75 | II | | 3 | CR | | SB |
| 6 | 63 | F | 60 | 8 | IIIA | S, CT | 3 | PR | | SB |
| 7 | 53 | M | 70 | 8 | IIIA | S, CT | 2 | PR | | SB |

TABLE 9-continued

Patient characteristics of stomach cancer

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 8 | 58 | M | 60 | 5 | IV | S, CT | 2 | NC | | RL, MT |
| 9 | 47 | M | 70 | 8 | II | S, CT | 3 | PR | | SB |
| 10 | 54 | M | 60 | 8 | IIIB | S, CT | 2 | MR | NS, I | MT |
| 11 | 81 | M | 60 | 4 | IV | S, CT | 2 | PD | | RL, MT |
| 12 | 56 | M | 60 | 9 | II | S, CT | 2 | PR | | SB |
| 13 | 46 | M | 60 | 5 | IV | S, CT | 2 | MR | | MT |
| 14 | 42 | M | 70 | 9 | IIIB | S, CT | 2 | MR | | MT |
| 15 | 56 | M | 80 | 0.5 | IIIA | | 3 | PR | | SB |
| 16 | 50 | M | 60 | 33 | IV | S, CT | 2 | NC | | RL, MT |
| 17 | 64 | F | 60 | 3 | IIIA | S | 3 | PR | | SB |
| 18 | 51 | M | 80 | 2.5 | IIIB | S, CT | 2 | MR | | SB |
| 19 | 82 | M | 60 | 0.75 | IIIB | | 2 | NC | | SB |
| 20 | 46 | M | 80 | 22 | IIIB | S, CT | 3 | PR | | SB |
| 21 | 48 | M | 60 | 3 | IV | S, CT | 2 | NC | | RL, MT |
| 22 | 45 | F | 60 | 30 | IV | S, CT | 2 | NC | | RL, MT |
| 23 | 56 | M | 60 | 26 | IV | S, CT | 2 | NC | | MT |
| 24 | 43 | M | 70 | 5 | II | S, CT | 2 | PR | | SB |
| 25 | 55 | M | 60 | 14 | IIIA | S, CT | 2 | MR | NS, I | SB |
| 26 | 67 | M | 80 | 8 | II | S, CT | 2 | PR | | SB |
| 27 | 41 | M | 60 | 0.5 | IV | | 2 | PD | | RL, MT |
| 28 | 45 | M | 80 | 1.5 | IIIA | S | 2 | PR | | SB |
| 29 | 51 | M | 100 | 0.5 | II | | 3 | CR | | SB |
| 30 | 64 | M | 90 | 3 | II | CT | 3 | CR | | SB |

[a]Interval between diagnosis of primary tumor and start of CHML treatment.
[b]Follow up since the trial start.
[c]PS, performance status (Karnofsky); S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT[+], glutamic-pyruvic transaminase increase; NS, nausea.

TABLE 10

Patient characteristics of head and neck cancer

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 1 | 43 | M | 80 | 2.5 | IVA | RT | 2 | PR | | SB |
| 2 | 65 | F | 70 | 2.5 | IVB | RT | 2 | PR | | SB |
| 3 | 36 | M | 60 | 38 | IVC | S, CT, RT | 3 | PR | | MT |
| 4 | 35 | M | 60 | 20 | IVC | S, CT, RT | 3 | PR | | MT |
| 5 | 38 | F | 70 | 36 | IVA | S, CT, RT | 2 | PR | | SB |
| 6 | 52 | F | 60 | 16 | IVA | S, CT, RT | 2 | PR | | SB |
| 7 | 49 | M | 70 | 0.5 | IVA | | 3 | PR | | SB |
| 8 | 47 | F | 90 | 0.25 | IIA | | 2 | CR | | SB |
| 9 | 31 | F | 60 | 0.5 | IVB | | 3 | PR | | SB |
| 10 | 42 | M | 80 | 6 | III | S, RT | 3 | CR | | SB |
| 11 | 50 | M | 70 | 0.5 | IVB | | 3 | PR | | SB |
| 12 | 61 | M | 80 | 5 | IIA | S, RT | 2 | PR | | SB |
| 13 | 24 | F | 60 | 8 | IVB | S, RT | 2 | PR | | SB |
| 14 | 35 | M | 80 | 0.5 | III | | 2 | PR | | SB |
| 15 | 32 | M | 60 | 18 | IVC | S, CT, RT | 2 | NC | | MT |
| 16 | 53 | F | 60 | 4 | IVA | S, CT | 2 | MR | | SB |
| 17 | 32 | M | 70 | 7 | IIB | S, RT | 2 | PR | | SB |
| 18 | 55 | M | 70 | 12 | IVB | S, CT | 2 | MR | | SB |
| 19 | 33 | M | 70 | 10 | IVA | S, RT | 3 | CR | | SB |
| 20 | 62 | M | 60 | 14 | IVA | S, CT | 2 | NC | | SB |
| 21 | 30 | F | 60 | 12 | IVB | S, CT, RT | 2 | MR | SGPT[+], I | SB |
| 22 | 36 | M | 70 | 0.5 | III | | 3 | PR | | SB |
| 23 | 66 | F | 70 | 7 | IIA | S, CT | 3 | CR | | SB |

[a]Interval between diagnosis of primary tumor and start of CHML treatment.
[b]Follow up since the trial start.
[c]PS, performance status (Karnofsky); S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT[+], glutamic-pyruvic transaminase increase; NS, nausea.

TABLE 11

Patient characteristics of leukemia

| Patient | Age | Sex | PS[c] | Interval[a] (months) | Clinical stage[20] | Previous treatment | No. of cycles | Response | Toxicity grade | Follow up[b] (6 months) |
|---|---|---|---|---|---|---|---|---|---|---|
| 1 | 19 | M | 80 | 0.5 | AML-M5 | | 2 | CR | | SB |
| 2 | 22 | M | 70 | 0.5 | ALL-L1 | | 3 | PR | | SB |
| 3 | 17 | F | 90 | 0.5 | ALL-L2 | | 3 | CR | | SB |
| 4 | 57 | M | 60 | 16 | CML | CT | 2 | MR | | SB |
| 5 | 21 | M | 80 | 0.5 | AML-M4 | | 3 | CR | | SB |
| 6 | 58 | M | 70 | 0.5 | CLL | | 3 | PR | | SB |
| 7 | 65 | M | 70 | 0.5 | CLL | | 2 | PR | | SB |
| 8 | 42 | M | 60 | 8 | AML-M2 | CT | 2 | PR | | SB |
| 9 | 15 | M | 70 | 0.5 | ALL-L1 | | 2 | PR | | SB |
| 10 | 38 | M | 80 | 0.5 | AML-M6 | | 2 | PR | | SB |
| 11 | 42 | M | 100 | 0.25 | CML | | 3 | CR | | SB |
| 12 | 50 | F | 60 | 12 | AML-M5 | CT | 2 | PR | | SB |
| 13 | 20 | M | 70 | 0.5 | ALL-L2 | | 2 | MR | SGPT[+], I | SB |
| 14 | 35 | M | 60 | 3 | AML-M1 | CT | 2 | NC | | SB |
| 15 | 62 | F | 60 | 18 | CLL | CT | 2 | PR | | SB |
| 16 | 45 | M | 70 | 26 | CML | CT | 2 | PR | | SB |
| 17 | 70 | M | 60 | 0.5 | CLL | | 2 | PR | | SB |
| 18 | 25 | M | 90 | 0.5 | AML-M2 | | 2 | PR | | SB |

[a]Interval between diagnosis of primary tumor and start of CHML treatment.
[b]Follow up since the trial start.
[c]PS, performance status (Karnofsky); AML, acute myelogenous leukemia; ALL, acute lymphoblastic leukemia; CML, chronic myelogenous leukemia; CLL, chronic lymphocytic leukemia; S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT[+], glutamic-pyruvic transaminase increase; NS, nausea.

TABLE 12

Patient characteristics of malignant lymphoma

| Patient[d] | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 1NHL | 28 | M | 70 | 32 | II | CT, RT | 2 | PR | | SB |
| 2NHL | 18 | F | 100 | 0.5 | II | | 3 | CR | | SB |
| 3HD | 32 | M | 60 | 41 | II | CT, RT | 2 | CR | | SB |
| 4NHL | 62 | M | 60 | 9 | IV | CT, RT | 2 | PD | | RL, MT |
| 5NHL | 53 | M | 80 | 28 | II | CT | 2 | CR | | SB |
| 6NHL | 47 | M | 70 | 18 | III | CT, RT | 2 | MR | | MT |
| 7NHL | 42 | M | 80 | 11 | II | CT, RT | 2 | CR | | SB |
| 8NHL | 29 | M | 70 | 28 | IV | CT, RT | 2 | PD | | RL, MT |
| 9NHL | 42 | M | 70 | 3 | II | CT | 3 | CR | | SB |
| 10NHL | 48 | M | 80 | 6 | III | CT, RT | 3 | CR | | SB |
| 11NHL | 55 | M | 80 | 12 | II | CT, RT | 2 | CR | | SB |
| 12HD | 16 | F | 90 | 4 | III | CT | 3 | CR | | SB |
| 13NHL | 64 | M | 80 | 20 | II | CT, RT | 2 | PR | | SB |
| 14NHL | 28 | F | 60 | 15 | IV | CT, RT | 2 | MR | | RL, MT |

[a]Interval between diagnosis of primary tumor and start of CHML treatment.
[b]Follow up since the trial start.
[c]PS, performance status (Karnofsky); S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT[+], glutamic-yruvic transaminase increase; NS, nausea.
[d]HD, Hodgkin disease;
[d]NHL, non-Hodgkin lymphoma.

TABLE 13

Patient characteristics of sarcoma

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 1 | 46 | M | 90 | 11 | III | CT, RT | 2 | MR | | MT |
| 2 | 31 | F | 70 | 8 | IIB | CT | 2 | PR | | SB |
| 3 | 49 | M | 80 | 10 | IIA | CT, RT | 2 | CR | | SB |
| 4 | 78 | M | 60 | 10 | III | CT, RT | 2 | NC | | RL, MT |
| 5 | 65 | F | 90 | 8 | III | CT | 2 | MR | | MT |

TABLE 13-continued

Patient characteristics of sarcoma

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 6 | 50 | M | 70 | 10 | III | CT, RT | 3 | PR | | SB |
| 7 | 61 | F | 80 | 9 | IV | CT, RT | 2 | PD | | RL, MT |

[a]Interval between diagnosis of primary tumor and start of CHML treatment.
[b]Follow up since the trial start.
[c]PS, performance status (Kamofsky); S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT+, glutamic-pyruvic transaminase increase; NS, nausea.

TABLE 14

Patient characteristics of malignant melanoma

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 1 | 64 | F | 80 | 0.5 | II | | 2 | PR | | SB |
| 2 | 35 | M | 90 | 0.5 | II | | 2 | CR | | SB |
| 3 | 41 | M | 70 | 11 | III | CT, RT | 2 | MR | | SB |

[a]Interval between diagnosis of primary tumor and start of CHML treatment.
[b]Follow up since the trial start.
[c]PS, performance status (Kamofsky); S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT+, glutamic-pyruvic transaminase increase; NS, nausea.

TABLE 15

Patient characteristics of myeloma

| Patient | Age | Sex | PS[c] | Interval[a] (months) | Clinical stage[18] | Previous treatment | No. of cycles | Response | Toxicity grade | Follow up[b] (6 months) |
|---|---|---|---|---|---|---|---|---|---|---|
| 1 | 68 | M | 60 | 16 | IIB | CT | 2 | MR | | SB |
| 2 | 54 | F | 70 | 12 | IIA | CT | 3 | PR | | SB |

[a]Interval between diagnosis of primary tumor and start of CHML treatment.
[b]Follow up since the trial start.
[c]PS, performance status (Kamofsky); S, surgery; RT, radiotherapy; CT, Chemotherapy; CR, a complete response; PR, a partial response; MR, a minor response; NC, no change; PD, progressive disease; SB, Stability with no relapse or no metastasis; RL, relapse; MT, metastasis; SGPT+, glutamic-pyruvic transaminase increase; NS, nausea.

Descriptions as above, include all the special terms, examples and figures, there is only for illustration of specificity of this invention in some extent. This total description is only for illustration and by no means of limitation.

However, it can be understood that there may be many modifications and variations in the changes of different forms, sizes, structures, components, purities and compositions of the present invention. However, the applicant do intend to include all such obvious modifications and variations within the scope of the invention which is defined by the following claims to be protected.

What is claimed is:

1. A method for treating cancer, comprising:
   administering to a patient in need thereof an effective amount of a pharmaceutical composition and a pharmaceutically acceptable carrier, the pharmaceutical composition consisting of:
   9-12 wt. % arachidonic acid;
   5-7 wt. % linolenic acid;
   12-26 wt. % docosahaenoic acid;
   8-14 wt. % eicosapentaenoic acid;
   28-38 wt. % oleic acid;
   8-15 wt. % palmitic acid;
   4-10 wt. % stearic acid;
   0.7-1.5 wt. % Vitamin A;
   0.3-1.0 wt. % Vitamin D;
   0.8-3.1 wt. % Vitamin E; and
   0.5-2.1 wt. % squalene.

2. The method of claim 1, wherein the cancer is cancer of liver, lung, skin, breast, brain glioma, colon and rectum, stomach, head and neck, leukemia, malignant lymphoma, sarcoma, malignant melanoma, or myeloma.

3. The method of claim 1, wherein the administering is performed by local injection, brain injection, arterial drip, or intravenous drip.

4. The method of claim 1, wherein the cancer is liver cancer.

5. The method of claim 1, wherein the cancer is lung cancer.

6. The method of claim 1, wherein the cancer is skin cancer.

7. The method of claim 1, wherein the cancer is breast cancer.

8. The method of claim 1, wherein the cancer is brain glioma.

9. The method of claim 1, wherein the cancer is colon and rectum cancer.

10. The method of claim 1, wherein the cancer is stomach cancer.

11. The method of claim 1, wherein the cancer is head and neck cancer.

12. The method of claim 1, wherein the cancer is leukemia.

13. The method of claim 1, wherein the cancer is malignant lymphoma.

14. The method of claim 1, wherein the cancer is sarcoma.

15. The method of claim 1, wherein the cancer is malignant melanoma.

16. The method of claim 1, wherein the cancer is myeloma.

* * * * *